(12) United States Patent
Lele

(10) Patent No.: US 8,476,404 B1
(45) Date of Patent: Jul. 2, 2013

(54) SELECTIVELY FUNCTIONALIZED POLYHYDRIC COMPOUNDS

(76) Inventor: Bhalchandra Shripad Lele, Newark, DE (US)

( * ) Notice: Subject to any disclaimer, the term of this patent is extended or adjusted under 35 U.S.C. 154(b) by 651 days.

(21) Appl. No.: 12/497,551

(22) Filed: Jul. 3, 2009

Related U.S. Application Data

(60) Provisional application No. 61/078,363, filed on Jul. 4, 2008.

(51) Int. Cl.
*C07K 17/06* (2006.01)
*C08F 265/06* (2006.01)

(52) U.S. Cl.
USPC ........... 528/407; 528/406; 514/429; 530/351; 424/78.27; 525/54.1

(58) Field of Classification Search
USPC 528/407, 406; 514/429; 530/351; 424/78.27; 525/54.1
See application file for complete search history.

(56) References Cited

U.S. PATENT DOCUMENTS

| | | | |
|---|---|---|---|
| 6,566,506 B2 * | 5/2003 | Greenwald et al. | 530/391.1 |
| 7,026,440 B2 * | 4/2006 | Bentley et al. | 528/407 |
| 7,176,325 B2 * | 2/2007 | Johnson et al. | 549/510 |
| 7,291,713 B2 * | 11/2007 | Yamasaki et al. | 530/351 |
| 7,316,811 B2 * | 1/2008 | Zhao et al. | 424/78.27 |

* cited by examiner

*Primary Examiner* — Elvis O Price

(57) ABSTRACT

This invention relates to polyhydric compounds containing primary and secondary hydroxyl groups selectively conjugated with linkers, polymers, and/or bioactive agents.

3 Claims, 7 Drawing Sheets

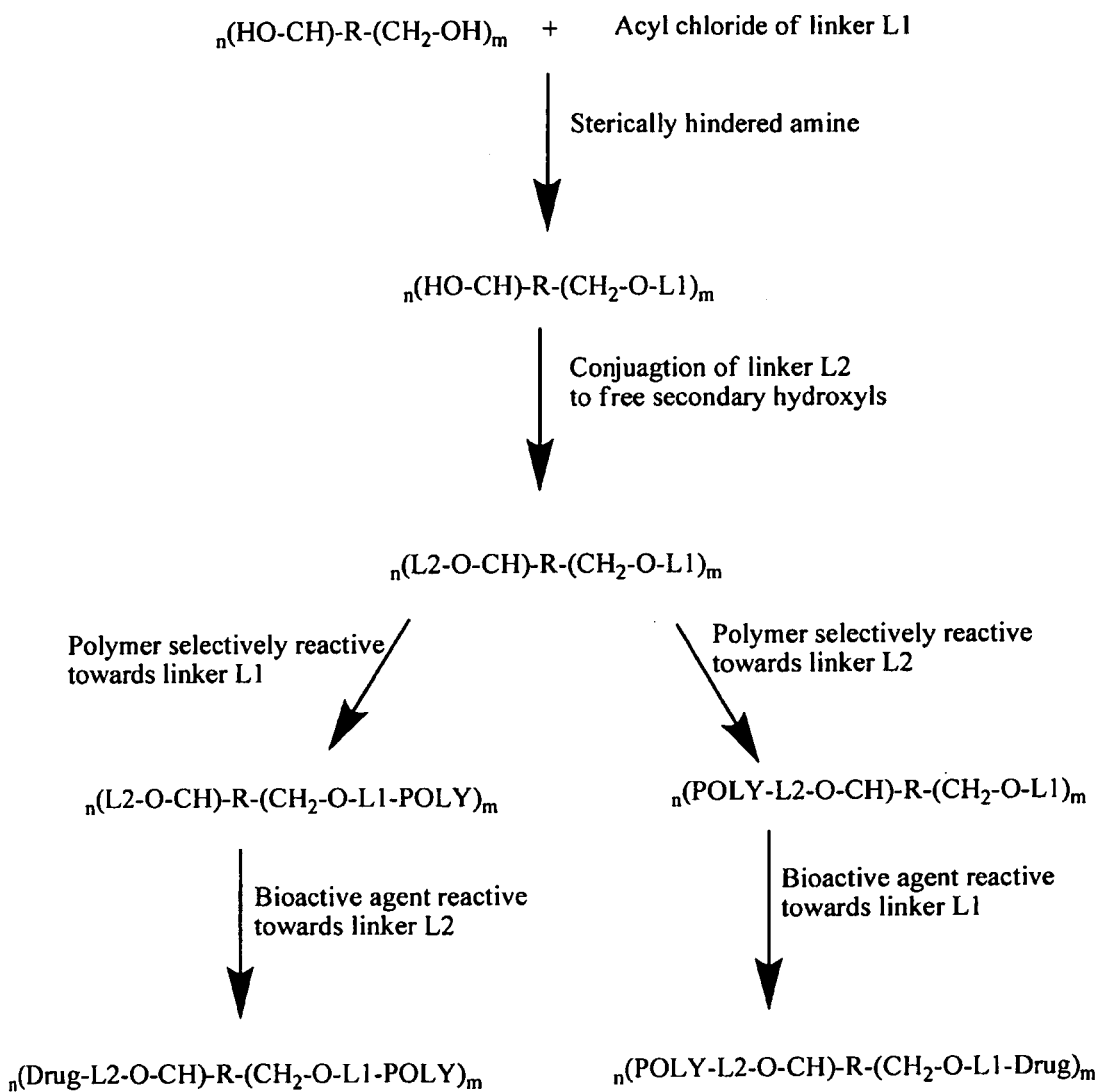
Figure 1: Schematic representation of the present invention

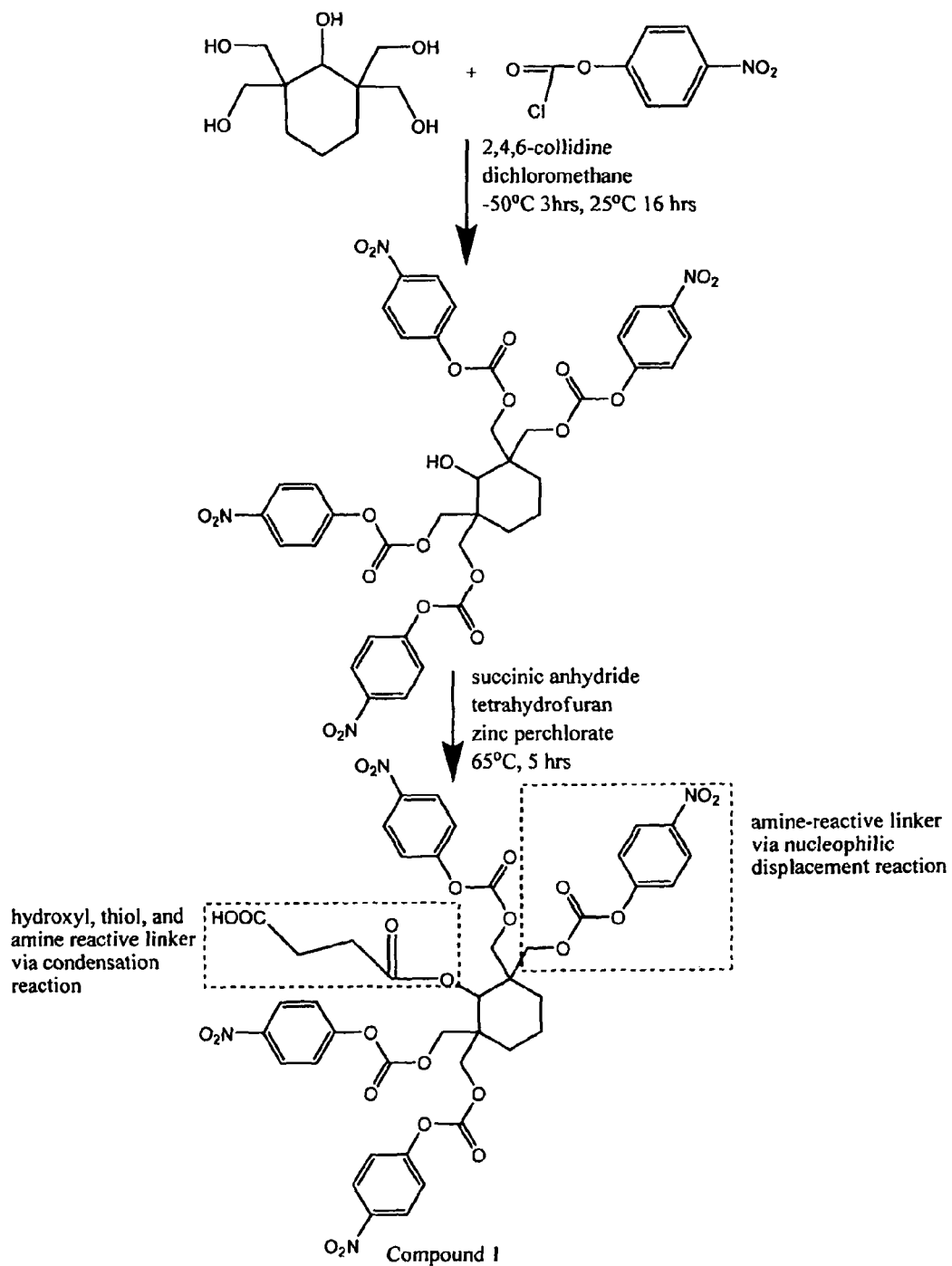
Figure 2: Synthesis of multifunctional building block- compound 1

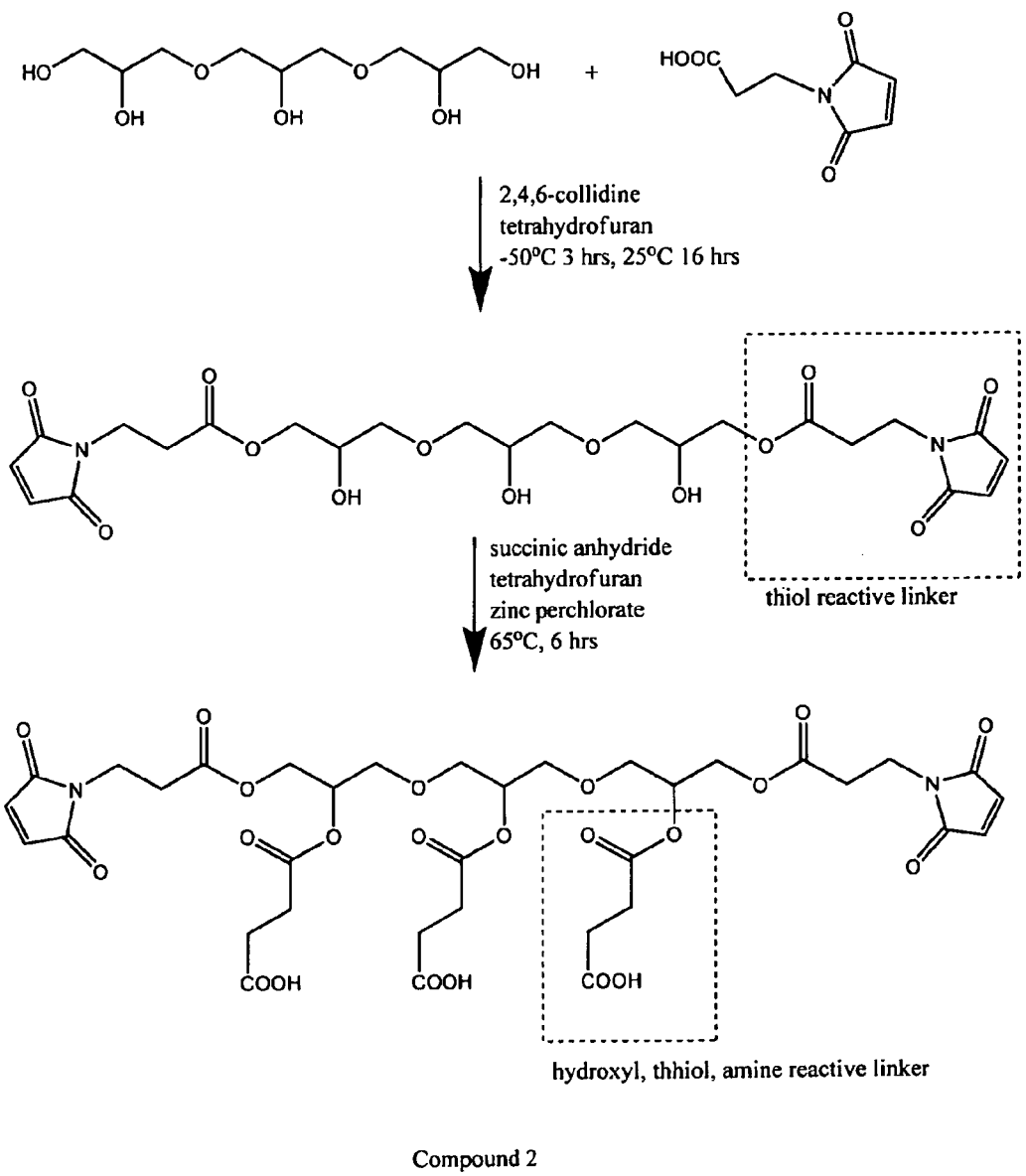
Compound 2
Figure 3: Synthesis of multifunctional building block- compound 2

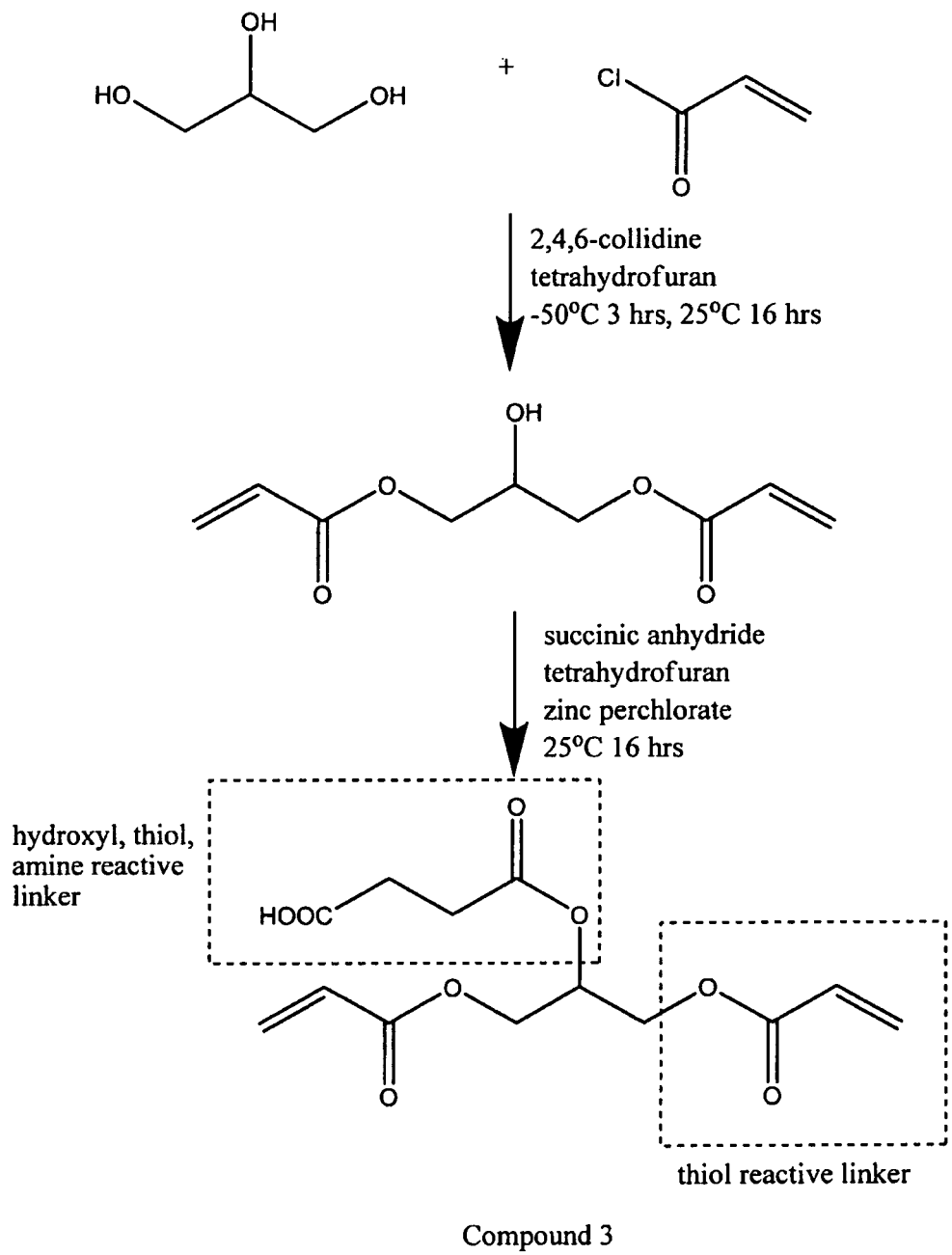
Figure 4: Synthesis of multifunctional building block- compound 3

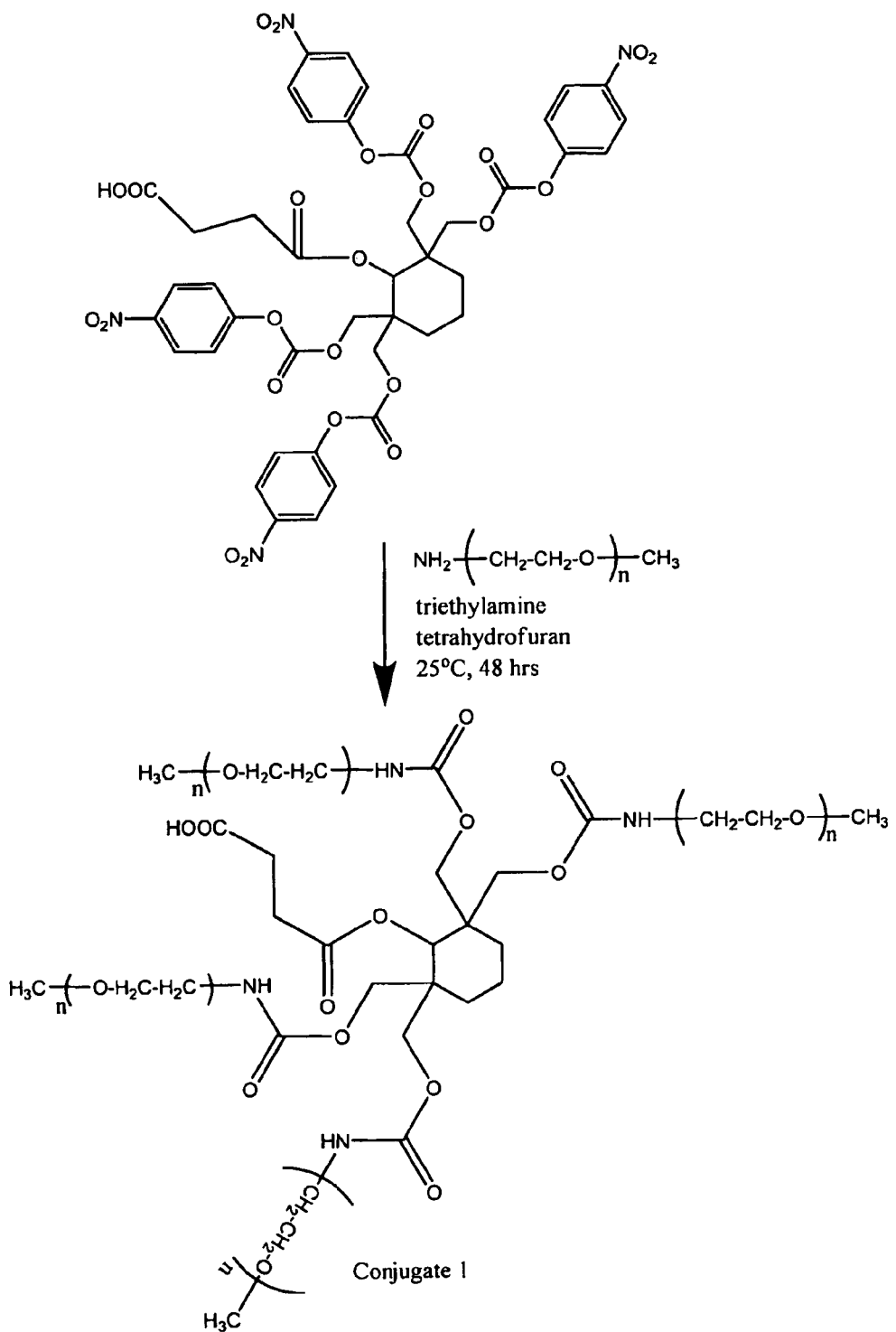
Figure 5: Synthesis of branched pegylation reagent (conjugate 1) using building block compound 1.

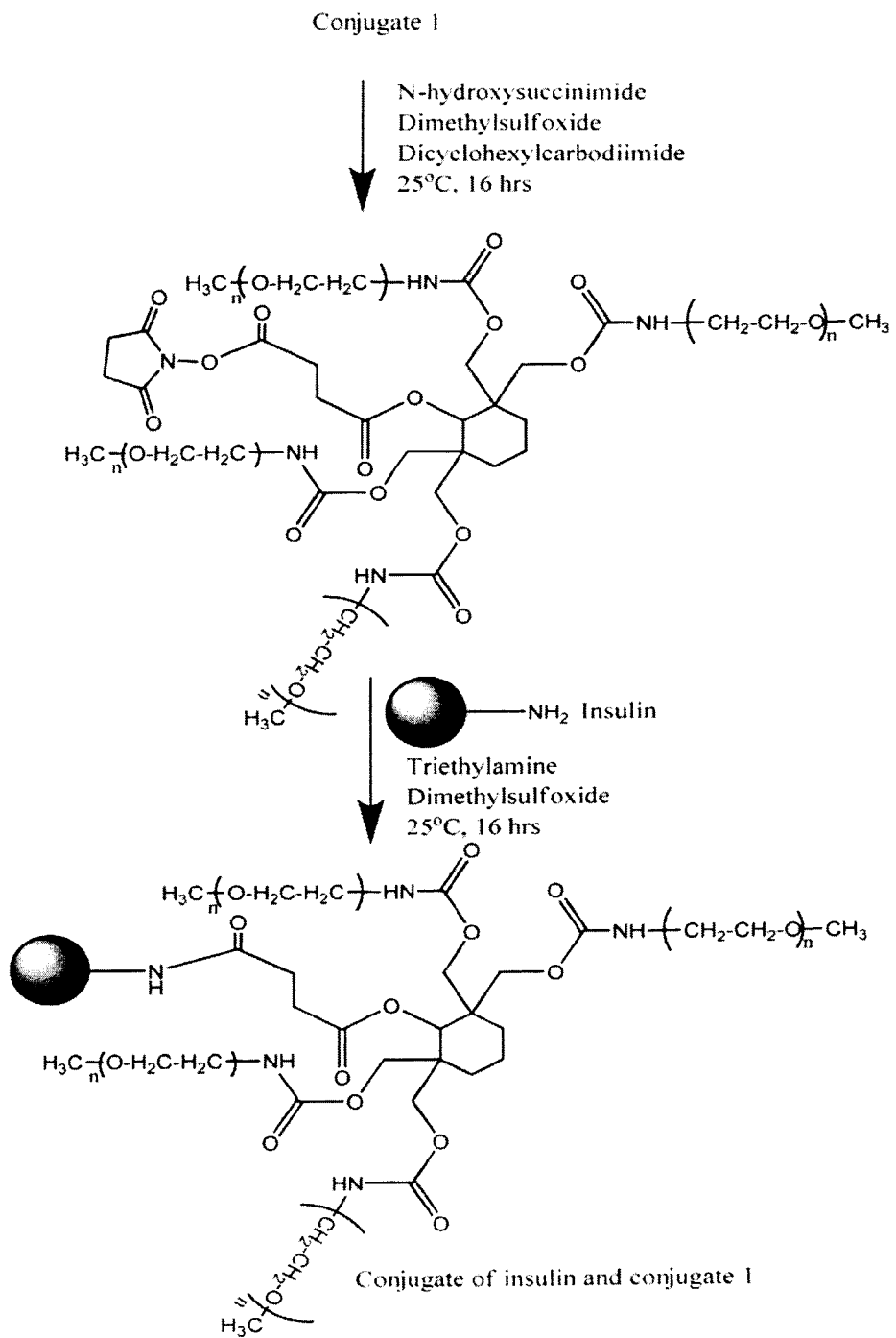
Figure 6: Synthesis of conjugate between a therapeutic agent and a branched pegylation reagent synthesized using building block compound 1.

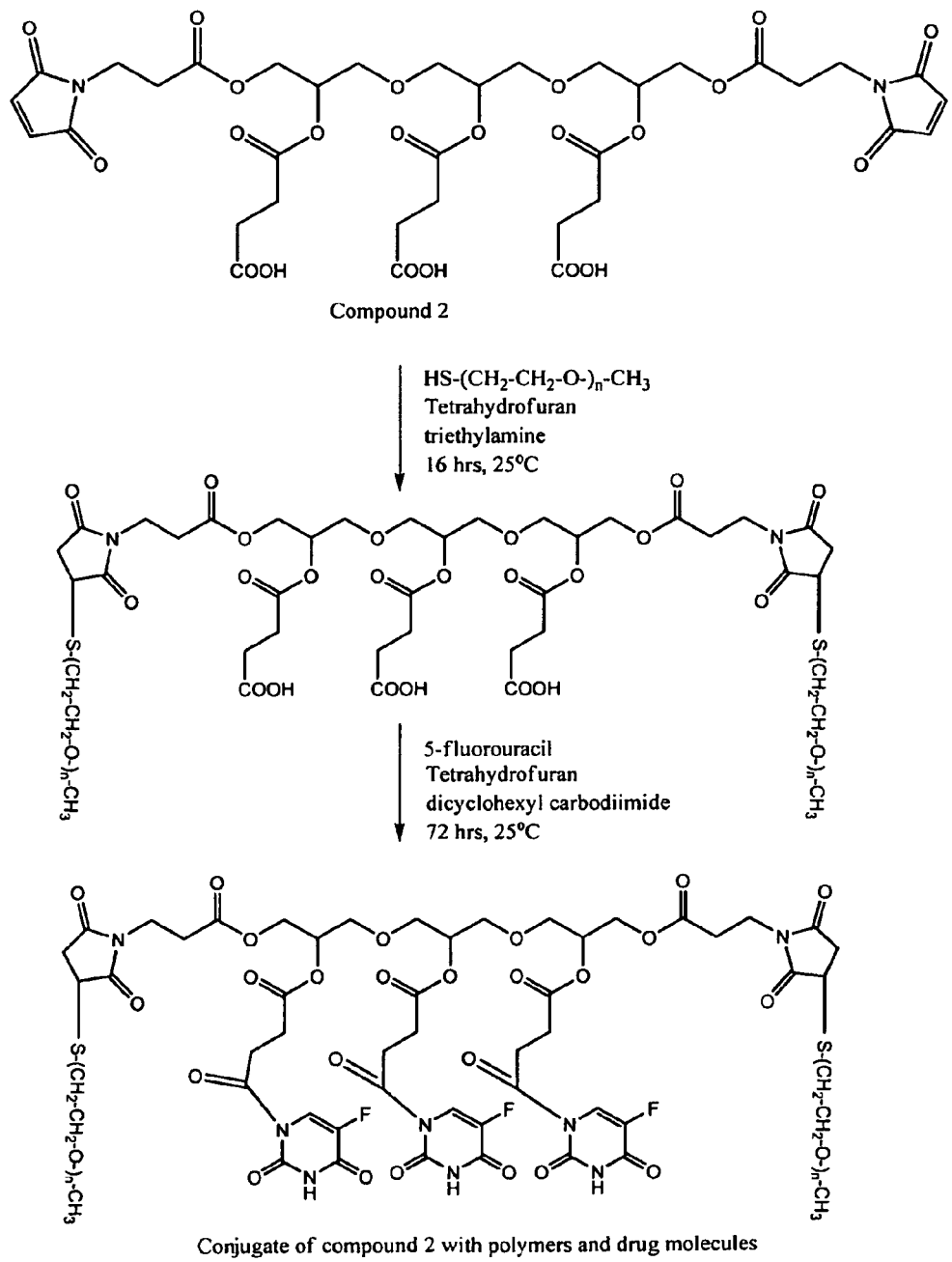
Figure 7: Synthesis of polyhydric compound selectively conjugated with multiple polymer and drug molecules.

SELECTIVELY FUNCTIONALIZED POLYHYDRIC COMPOUNDS

This application claims the benefit of U.S. Provisional Application No. 61/078,363 filed on Jul. 4, 2008.

SUMMARY OF THE INVENTION

This invention relates to polyhydric compounds containing primary and secondary hydroxyl groups selectively conjugated with linkers, polymers, and bioactive agents.

BACKGROUND OF THE INVENTION

Bioactive small molecules, proteins and peptides are routinely conjugated with water soluble polymers to increase their water solubility, circulation half life and decrease the antigenicity. Amongst many water soluble polymers poly(ethylene glycol) (PEG) is particularly useful in modification of pharmaceutically active compounds, proteins and peptides. "Pegylated" conjugates often display improved pharmacokinetic properties than native bioactive agents. A rich variety of pegylation reagents is commercially available for chemical modification of bioactive agents. Linear, branched, star shaped, and multi-arm pegylation reagents all have been used [Harris J M, Chess R B. Effect of pegylation on pharmaceuticals. Nature 2003; 2: 214-221; Vicent M J, Duncan R. Polymer conjugates: Nanosized medicines for treating cancer. Trends in Biotechnol. 2006; 24: 39-47; Duncan R. The dawning of polymer therapeutics. Nature Rev. Drug Discovery 2003; 2: 347-360; Sheffield W P. Modification of clearance of therapeutic and potentially therapeutic proteins. Current Drug Targets—Cardiovas. & Hemat. Dis. 2001; 1: 1-22; Veronese F M, Pasut G. PEGylation, successful approach to drug delivery. Drug Deliv. Today 2005; 10: 1451-1458; Mehvar R. Modulation of pharmacokinetics and pharmacodynamics of proteins by polyethylene glycol conjugation. J. Pharm. Pharmceut. Sci. 2000; 3: 125-136; Kozlowski A, Harris J M. Improvements in protein PEGylation: pegylated intereferons for treatment of hepatitis C. J. Controlled Rel. 2001; 72: 217-224].

Branched pegylation reagents have proven to be particularly useful over linear pegylation reagents as these reagents provide either multiple sites for conjugation of bioactive molecules or multiple PEG chains conjugated per bioactive molecule. Also, once conjugated to a therapeutic, the branched polymers have provided longer circulation times than that provided by linear polymers. However, syntheses of multi-arm or branched pegylation reagents described in the prior art has involved use of tedious purification procedures and laborious chemistries of protection and deprotection of multiple functional groups that need to be modified with either PEG chains or bioactive molecules. Also despite such tedious chemistries, the reagents described in the prior art have had very few attachment points for polymers and bioactive agents.

For example, U.S. Pat. No. 7,291,713 describes preparation of three chain-branched pegylation reagents by modifying pentaerythritol which contains four primary hydroxyl groups. According to this invention, an excess of PEG is conjugated to pentaerythritol and a fraction in which PEG is conjugated to only three out of four available hydroxyl groups is isolated by column chromatography. Then the remaining hydroxyl group is modified with a linker to prepare the final, branched pegylation reagent.

Another U.S. Pat. No. 7,316,811 describes multiarm PEG-polypeptide block copolymers for conjugating multiple drug molecules to polymer carriers. According to this invention, a block copolymer between 8-arm PEG and poly(benzyl aspartate) or poly(benzyl glutamate) is first prepared. Benzyl groups on block copolymer are deprotected and the drug is conjugated with free carboxyl groups of poly(aspartic acid) or poly(glutamic acid) segment in the block copolymer.

U.S. Pat. No. 6,566,506 describes branched PEG reagent synthesized by conjugating two primary amino groups in 1,3-diamino-2-propanol selectively with PEG chains and the secondary hydroxyl group with para-nitrophenyl chloroformate, without applying protection-deprotection chemistries. The branched PEG reagent was synthesized by exploiting reactivity differences between amino and hydroxyl groups in conjugation reactions. However, the limitations in using commonly available amino alcohols as starting molecules for synthesis of branched PEG reagents is that these amino alcohols contain very few attachment sites for polymers and bioactive agents.

Yet another U.S. Pat. No. 7,026,440 describes preparation of multiarm pegylation reagents using hydrocarbon moieties with multiple functional groups attached to PEG chains and a linker moiety capable of conjugating at a single point. Glycerol is the preferred hydrocarbon used here. Secondary hydroxyl groups in glycerol were first protected and PEG chains were grown from the two free primary hydroxyls via ethylene oxide polymerization. The terminal hydroxyls on grown PEG chains were then protected, the secondary hydroxyl was deprotected, and a linker was finally attached. Briefly, this chemistry provides reagents containing multiple PEG chains and a single attachment site within a single molecule. Reagents that provide multiple PEG chains and multiple sites for attachment of bioactive agents are not achievable from this art.

In summary, prior art provides limited structural and conformational variety of central aliphatic core in branched pegylation reagents and few sites for attachment of bioactive agents. The main reason for this shortcoming is lack of multifunctional, core forming molecules to which polymers and biomolecules can be conjugated selectively and preferably with simpler chemistries. It is therefore the object of this invention to provide a simple method for synthesis of multifunctional, activated building blocks. It is also the object of this invention to provide such multifunctional, activated building blocks and their conjugates with polymers and bioactive agents.

DESCRIPTION OF THE INVENTION

Polyhydric alcohols containing a large number of primary and secondary hydroxyl groups in the same molecule are very attractive materials to synthesize the above mentioned building blocks and their conjugates with polymers and bioactive agents. Moreover, the difference in the reactivity of primary and secondary hydroxyl groups in such alcohols provides an opportunity to devise a simpler chemistry preferably without use of protecting groups. Polyhydric alcohols are also available in different shapes such as cyclic, bicyclic, linear etc. which would allow preparation of pegylation reagents in many conformations not known in the prior art Ishihara et al [Ishihara, K.; Kurihara, H.; Yamamoto, H. *J. Org. Chem.* 1993: 58, 3791-3793] reported selective acetylation of primary hydroxyl groups in compounds containing both primary and secondary hydroxyl groups without use of protecting groups. Acetyl chloride was reacted with polyhydric compounds containing both primary and secondary hydroxyl groups in the presence of sterically hindered amines. It was found that in the presence of sterically hindered amines, >99% acetylation of primary hydroxyl groups took place leaving secondary hydroxyl groups unmodified. Recently, this basic finding was utilized in U.S. Pat. No. 7,176,325 for selective acylation of anticancer taxanes at C-2' position.

We have exploited this exclusive acylation at primary hydroxyl groups in presence of sterically hindered amines to selectively modify polyhydric alcohols at primary hydroxyl positions with various linkers. The free secondary hydroxyl groups in these polyhydric compounds are then attached with different linkers and multifunctional, activated building blocks are obtained. This is schematically illustrated in FIG. 1. Differences in the reactivity of linkers are then exploited to attach polymers and bioactive agents at desired primary or secondary hydroxyl positions. Based on these finding a new family of selectively functionalized polyhydric alcohols is claimed herein.

Present invention provides building blocks in different shapes with multiple attachment sites not only for polymers but also for bioactive agents with a choice to select the conjugation site within a single, core molecule. The prior art does not provide all these features either in chemistries or in aliphatic cores used.

Following embodiments describe the present invention in more details:

In an embodiment of the present invention, polyhydric alcohol is selected from compounds containing both primary and secondary hydroxyls in the same molecule including 1,2,6-hexane triol, 1,2,4-butane triol, glycerol, hyper branched glycerol, triglycerol, tetraglycerol, pentaglycerol, 2,2,6,6-tetrakis(hydroxymethyl)cyclohexanol, 3-bromo-1,2-propanediol, 3-Chloro-1,2-propanediol, 1,3-butanediol, 1,2-butanediol, 1,2,4-butanetriol, 2-hydroxymethyl-1,3-propanediol, DL-threitol, 1,2-pentanediol, 1,4-pentanediol, 3-methyl-1,3-butanediol, 1,2-hexanediol, 1,5-hexanediol, 1,2,6-hexanetriol, α,α'-diglycerol, 3-tert-butoxy-1,2-propanediol, 1-phenyl-1,2-ethanediol, 1-phenyl-1,2-ethanediol, 1,2-octanediol, 2-ethyl-1,3-hexanediol, 1,2,7,8-octanetetrol, 1-(4-nitrophenoxy)-2,3-propanediol, 4-hydroxy-3-methoxyphenylglycol, 3-benzyloxy-1,2-propanediol, mephenesin, 1,2-dodecanediol, 1,2-hexadecanediol, 1-O-palmityl-glycerol, and batyl alcohol.

In another embodiment, the linker for attachment with primary or secondary hydroxyl groups are selected from compounds capable of forming ester, amide, carbonate, ether, and carbamate bonds including p-nitrophenyl chloroformate, succinic anhydride, chloroacetyl chloride, triphosgene, 2-bromoacetic acid, 3-bromopropionic acid, N-hydroxysuccinimidyl chloroformate, 3-maleimidopropionic acid, formyl benzoic acid and carboxyl terminated enzymatically degradable peptides.

In another embodiment, sterically hindered amine used as base in reaction between polyhydric alcohol and acyl chloride of linker is selected from group consisting compounds such as 2,3,5-collidine, 2,4,6-collidine, 2,6-di-tert-butylpyridine, 2-6-di-tert-butyl-4-(dimethylamino)pyridine, 2,6 di-methyl-4-(dimethylamino)pyridine, 2,3-lutidine, 2,4-lutidine, 2,5-lutidine, 2,6-lutidine, 2,3,5,6-tetramethylpyridine, N-tert-butylmorpholine, N,N-diisopropylethylamine, N,N-diisopropylisobutylamine, N-ethyldicyclohexylamine, triethylamine, triisopropylamine, tripropylamine, imidazole, 1,5-diazabicylo[4.3.0]non-5-ene (DBN), 1,4-diazabicylo[2.2.2.]octane (Dabco), 1,8-diazabicylo[5.4.0]undec-7-ene (DBU) etc.

In another embodiment, water soluble polymer for conjugation with polyhydric alcohol-linker conjugate is selected from a group of substantially biocompatible polymers consisting poly(ethylene glycol), poly(ethylene oxide)-block-poly(propylene oxide), poly(N-2-hydroxypropylmethacrylamide), poly(N-vinylpyrrolidone), poly(2-methacryloyloxyethyl phosphorylcholine), poly(2-ethyl oxazoline), poly(N-isopropylacrylamide), poly(N-acryloyl morpholine), and combinations thereof.

In yet another embodiment, water soluble polymer has terminal nucleophilic groups including amine, thiol or hydroxyl group which are capable of forming conjugates with linkers.

In another embodiment, bioactive agent for conjugation with polyhydric alcohol-linker conjugate is selected from small molecules, proteins and peptides.

Example 1

Compound 1

In a round bottom flask, 2,2,6,6-tetrakis(hydroxymethyl) cyclohexanol (2.2 g, 0.01 mole), 2,4,6-collidine (4.84 g, 0.04 mole) is dissolved in 100 mL dichloromethane. The reaction mixture is cooled to −50° C. To this, p-nitrophenyl chloroformate (8.04 g, 0.04 mole) dissolved in 50 mL dichloromethane is added in dropwise manner. The reaction mixture is warmed up to room temperature (25° C.) and stirred overnight. Collidine.hydrochloride salt is filtered. To the clear solution, tetrahydrofuran, succinic anhydride (1.0 g, 0.01 mole) and zinc perchlorate (20 mg) is added. The reaction mixture is stirred for 5 hrs at 65° C. and concentrated in vacuum. Compound 1 is isolated by reprecipitation from dichloromethane into hexane. Reaction scheme is shown in FIG. 2.

Example 2

Compound 2

In a round bottom flask, triglycerol (2.4 g, 0.01 mole), 2,4,6-collidine (2.42 g, 0.02 mole) is dissolved in 100 mL tetrahydrofuran. The reaction mixture is cooled to −50° C. To this, 3-maleimidopropinoyl chloride (3.7 g, 0.02 mole) dissolved in 50 mL tetrahydrofuran is added in dropwise manner. The reaction mixture is warmed up to room temperature (25° C.) and stirred overnight. Collidine.hydrochloride salt is filtered. To the clear solution, tetrahydrofuran, succinic anhydride (3.0 g, 0.03 mole) and zinc perchlorate (60 mg) is added. The reaction mixture is stirred for 6 hrs at 65° C. and concentrated in vacuum. Compound 2 is isolated by reprecipitation from tetrahydrofuran into hexane. Reaction scheme is shown in FIG. 3.

Example 3

Compound 3

In a round bottom flask, glycerol (0.92 g, 0.01 mole), 2,4,6-collidine (2.42 g, 0.02 mole) is dissolved in 100 mL tetrahydrofuran. The reaction mixture is cooled to −50° C. To this, acryloyl chloride (1.8 g, 0.02 mole) dissolved in 50 mL tetrahydrofuran is added in dropwise manner. The reaction mixture is warmed up to room temperature (25° C.) and stirred overnight. Collidine.hydrochloride salt is filtered. To the clear solution, succinic anhydride (1.0 g, 0.01 mole) and zinc perchlorate (20 mg) is added. The reaction mixture is stirred for 16 hrs at 25° C. and concentrated in vacuum. Compound 3 is isolated by reprecipitation from tetrahydrofuran into hexane. Reaction scheme is shown in FIG. 4.

Example 4

Polyethylene Glycol-Compound 1 Conjugate (Conjugate 1)

Compound 1 (0.84 g, 0.001 mole), methoxypoly(ethylene glycol)amine of MW 2 kDa (8.0 g, 0.004 mole), triethylamine (0.5 ml) are dissolved in 100 mL tetrahydrofuran. The reaction mixture is stirred at 25° C. for 48 hrs. Polyethylene glycol-compound 1 conjugate is isolated by reprecipitation from tetrahydrofuran into diethyl ether. Reaction scheme is shown in FIG. 5.

Example 5

Therapeutic Composition Containing Insulin Conjugated to Conjugate 1

Conjugate 1 (1.5 g, 0.0002 mole), N-hydroxysuccinamide (0.02 g, 0.0002 mole), dicyclohexylcarbodiimide (0.04 g, 0.0002 mole) are dissolved in dimethylsulfoxide and stirred at 25° C. for 16 hrs. The reaction mixture is filtered to remove precipitated dicyclohexylurea. Insulin (1.0 g, 0.0002 mole), triethylamine (0.05 mL) is added and the reaction mixture is stirred for 16 hrs at 25° C. Insulin conjugated with conjugate 1 is isolated by reprecipitation from dimethylsulfoxide into diethyl ether. Reaction scheme is shown in FIG. 6.

Examples 6

Conjugate of Compound 2 with Polymers and Drug Molecules

Compound 2 (0.622 g, 0.001 mole), methoxy(polyethylene glycol)-thiol of molecular weight 2000 (4.0 g, 0.002 mole) triethylamine (0.5 mL) is dissolved in 40 mL tetrahydrofuran. The solution is stirred at room temperature for 16 hrs. PEG-compound 2 conjugate is isolated by reprecipitation from THF into ether. PEG-compound 2 conjugate (4.6 g 0.001 mole), 5-fluorouracil (0.39 g, 0.003 mole), dicyclohexylcarbodiimide (0.618 g, 0.003 mole) are dissolved in 30 ml THF and stirred at room temperature for 3 days. Reaction mixture is filtered to remove dicyclohexylurea. Clear solution is poured in diethyl ether to precipitate the product—PEG-compound 2-5-fluorouracil. Reaction scheme is shown in FIG. 7.

What is claimed is:

1. Conjugates of water soluble polymers with compounds of formula (I) wherein water soluble polymers are covalently attached via linker L1 or L2

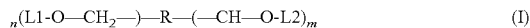

$$_n(\text{L1-O-CH}_2\text{-})\text{-R-}(\text{-CH-O-L2})_m \quad (I)$$

wherein R is hydrocarbon in polyhydric alcohols containing at least one primary hydroxyl group and at least one secondary hydroxyl group selected from group of alcohols comprising 1,2,6-hexanetriol, 1,2,4-butanetriol, glycerol, triglycerol, tetraglycerol, pentaglycerol, hexaglycerol, polyglycerol, 2,2,6,6-tetrakis(hydroxymethyl)cyclohexanol, 3-Bromo-1,2-propanediol, 3-Chloro-1,2-propanediol, 1,3-butanediol, 1,2-butanediol, 2-hydroxymethyl-1,3-propanediol, DL-threitol, 1,2-pentanediol, 1,4-pentanediol, 3-Methyl-1,3-butanediol, 1,2-hexanediol, 1,5-hexanediol, 1,2,6-hexanetriol, α,α'-diglycerol, 3-tert-butoxy-1,2-propanediol, 1-phenyl-1,2-ethanediol, 1-phenyl-1,2-ethanediol, 1,2-octanediol, 2-ethyl-1,3-hexanediol, 1,2,7,8-octanetetrol, 1-(4-nitrophenoxy)-2,3-propanediol, 4-hydroxy-3-methoxyphenylglycol, 3-benzyloxy-1,2-propanediol, mephenesin, 1,2-dodecanediol, 1,2-hexadecanediol, 1-O-palmitylglycerol, batyl alcohol and the likes;

L1 and L2 are linkers conjugated to hydroxyl groups in polyhydric alcohols and capable of undergoing further conjugation selected from group of linkers comprising N-hydroxysuccininimidyl esters, maleimidoalkanoic acids, succinic acid, succinic anhydride, p-nitrophenylchloroformate, formyl benzoic acid, isocyanates, diisocyanates, isothiocyanates, diisothiocyantes, aminoalkanoic acids, thioalkanoic acids, acetals, ketals, sulfones acrylates, methacrylates, alkyl chlorides, acyl chlorides, aldehydes and the likes and n and m are integers from 1 to 12.

2. Conjugates of claim 1 wherein water soluble polymer is selected from group of water soluble and substantially biocompatible polymers comprising polyethylene glycol, poly(ethylene oxide), poly(ethylene oxide)-block-poly(propylene oxide), poly(N-2-hydroxypropylmethacrylamide), poly(N-vinylpyrrolidone), poly(methacryloyloxyethyl phosphorylcholine), poly(monomethoxy-polyethylene glycol-methacrylate), poly(acrylic acid), poly(methacrylic acid), poly(styrene-co-maleic anhydride), and poly(N,N-dimethyl aminoethyl methacrylate), poly(2-hydroxyethyl methacrylate), poly(2-ethyl oxazoline), poly(N-acryloyl morpholine), and poly(N-isopropylacrylamide).

3. Conjugates of claim 2 wherein water soluble polymers are capped at the terminals not conjugated to polyhydric alcohols with functional groups capable of undergoing electrophilic or nucleophilic reactions selected from group comprising hydroxyl, carboxyl, amino, thio, aldehyde, acetal, ketal, sulfone, acrylate, methacrylate, p-nitrophenyl chloroformyl, maleimidyl, N-hydroxysuccinimidyl, formylbenzoyl, succinyl, succinimidyl pyridyl dithiopyridyl, isocyanato, isothioacyanato and the likes.

* * * * *